United States Patent [19]

Doyle et al.

[11] Patent Number: 5,059,785
[45] Date of Patent: Oct. 22, 1991

[54] BACKSCATTERING SPECTROMETRY DEVICE FOR IDENTIFYING UNKNOWN ELEMENTS PRESENT IN A WORKPIECE

[75] Inventors: Barney L. Doyle; James A. Knapp, both of Albuquerque, N. Mex.

[73] Assignee: The United States of America as represented by the United States Department of Energy, Washington, D.C.

[21] Appl. No.: 530,672

[22] Filed: May 30, 1990

[51] Int. Cl.$^5$ .............................................. H01J 37/26
[52] U.S. Cl. .................................... 250/309; 250/307
[58] Field of Search ........... 250/306, 307, 309, 492.21, 250/505.1

[56] References Cited

U.S. PATENT DOCUMENTS

| | | | |
|---|---|---|---|
| 3,916,191 | 10/1975 | Leys et al. | 250/306 |
| 4,449,051 | 5/1984 | Berkowitz | 250/492.2 |
| 4,494,005 | 1/1985 | Shibata et al. | 250/492.2 |
| 4,687,930 | 8/1987 | Tamura et al. | 250/309 |
| 4,748,325 | 5/1988 | Slodzian | 250/309 |
| 4,766,313 | 8/1988 | Homma et al. | 250/309 |
| 4,829,179 | 5/1989 | Aoki et al. | 250/309 |
| 4,849,629 | 7/1989 | Daimon et al. | 250/305 |
| 4,967,078 | 10/1990 | Purser | 250/309 |

OTHER PUBLICATIONS

R. Hart et al., "The Detection Sensitivity of Heavy Impurities In Si Using 280 keV He$^{2+}$ and C$^{2+}$ Back-Scattering", *Thin Solid Films*, vol. 19, 1973, pp. 137–144.
B. Cordts et al., "Contamination Control In SIMOX Implanters", *Materials Research Society Symposium Proceedings*, vol. 107, 1968, Materials Research Society, pp. 147–150.
B. Doyle et al., "Heavy Ion Backscattering Spectrometry (HIBS)—An Improved Technique For Trace Element Detection", *Nuclear Instruments and Methods in Physics Research*, vol. B42, 1989, pp. 295–297.
J. Knapp et al., "Heavy-Ion Backscattering Spectrometry (HIBS) For High-Sensitivity Surface Impurity Detection", *Nuclear Instruments and Methods In Physics Research*, vol. B45, 1990, pp. 143–146.

*Primary Examiner*—Bruce C. Anderson
*Attorney, Agent, or Firm*—Karla Ojanen; James H. Chafin; William R. Moser

[57] ABSTRACT

A backscattering spectrometry method and device for identifying and quantifying impurities in a workpiece during processing and manufacturing of that workpiece. While the workpiece is implanted with an ion beam, that same ion beam backscatters resulting from collisions with known atoms and with impurities within the workpiece. Those ions backscatter along a predetermined scattering angle and are filtered using a self-supporting filter to stop the ions with a lower energy because they collided with the known atoms of the workpiece of a smaller mass. Those ions which pass through the filter have a greater energy resulting from impact with impurities having a greater mass than the known atoms of the workpiece. A detector counts the number and measures the energy of the ions which pass through the filter. From the energy determination and knowledge of the scattering angle, a mass calculation determines the identity, and from the number and solid angle of the scattering angle, a relative concentration of the impurity is obtained.

14 Claims, 1 Drawing Sheet

BACKSCATTERING SPECTROMETRY DEVICE FOR IDENTIFYING UNKNOWN ELEMENTS PRESENT IN A WORKPIECE

RIGHTS OF THE GOVERNMENT

The U.S. Government has rights in this invention pursuant to Contract No. DE-AC04-76DP00789 between the U.S. Department of Energy and AT&T Company.

BACKGROUND OF THE INVENTION

1. Field of the Invention

The present invention relates generally to the field of semiconductor manufacturing and, more particularly, to a device and method for in-situ identification and quantification of elements having a higher atomic weight that the elements of a workpiece for on-line diagnostics of purity and content of the substrate.

2. Description of the Prior Art

The ability to routinely measure very small levels of contaminant elements in a workpiece is increasingly important in the area of microelectronics as integrated circuit device sizes become ever smaller. In the microelectronics area, for example, as few as $10^{11}-10^{12}/cm^2$ of heavy metal contaminant elements in a silicon workpiece can create major problems with the gate oxide in manufactured MOS devices by greatly reducing the oxide breakdown strength.

Devices are available for identifying unknown contaminant elements in a workpiece. One device, which is used extensively, is the Rutherford Backscattering Spectrometry (RBS) device which detects and identifies unknown contaminant elements in a workpiece having a mass greater than the mass of the primary element forming the workpiece. The RBS device employs a high energy ion beam (typically a one to two MeV He+ ion beam) that impacts the surface of a workpiece. The ions from the beam collide with the atoms near the surface of the workpiece and are scattered with a measurable energy and momentum. A portion of the backscattered high energy ion beam is directed towards a detector. The detector counts the backscattered ions and measures their energies which enables the identification and quantification of contaminant elements present in the workpiece.

Although the Rutherford Backscattering Spectrometry device provides one means for identifying unknown contaminant elements in a workpiece, it has major limitations. One limitation of the RBS device is that the use of ion beams at high energies, 1 to 2 MeV, eventually damages the detector.

Another limitation is its sensitivity or the ability to detect small concentrations of the unknown contaminant elements present in the workpiece. The small cross sections (typically less than 0.1 to 10 barns) for scattering from the unknown contaminants coupled with the interference of background noise introduced at the detector because of pulse pileup preclude greater sensitivity. For example, a none to two MeV He+ ion beam used according to the principles of the RBS device to analyze a silicon workpiece has an average sensitivity of approximately $10^{13}$ atoms/cm$^2$.

The sensitivity of a RBS device may be increased by increasing the cross-section for scattering where the cross-section is a parameter of probability of a particular process, in this case, a collision between particles in the ion beam and atoms in the workpiece. The cross-section for scattering is proportional to $(Z_1E_0)^2$, where $Z_1$ is the atomic number of the ion beam and $E_0$ is the incident energy of the ion beam. Thus, increasing the cross-section may be accomplished either by decreasing the energy level of the ion beam, increasing the atomic number of the ion beam, or by doing both (using a heavier ion beam at a lower energy level to impact the surface of a workpiece). For example, using a four hundred (400) KeV C+ ion beam instead of a two (2) MeV He+ ion beam increases the sensitivity approximately two hundred and twenty five (225) times. Although the sensitivity of the RBS device may be increased by decreasing the energy level of the ion beam or increasing its atomic number, these techniques have not been widely exploited because the increased number of generally lower energy, backscattered ions from the workpiece saturate the detector and preclude detection of ions backscattered from any heavier mass unknown contaminant elements. In order to protect the detector utilized to count ions backscattered from the workpiece and from contaminant element atoms in the "increased sensitivity" situation, both pulse pileup rejection circuitry and a cooling system for the detector are required.

Consequently, a need exists for an improved backscattering spectrometry method and device which, while a workpiece is being implanted with an ion beam, prevents lower energy backscattered ions from the workpiece atoms from saturating the detector to preclude or "overwhelm" the detection of higher energy ions backscattered from unknown contaminant elements. The measurement of the energy and number of these ions enable the identification of the contaminant elements based on their mass. Preferably, the sensitivity of the backscattering spectrometry device should be increased without requiring the use of presently needed pulse pileup rejection circuitry and/or a cooling system for the detector. And ideally, the device and method provides for on-line or in-situ diagnostics wherein the same beam that is used for implantation during the manufacturing of semiconductor devices is used for monitoring the level and kind of contamination.

SUMMARY OF THE INVENTION

The present invention relates to a backscattering spectrometry device and a method for performing backscattering spectrometry designed to satisfy the aforementioned needs. The backscattering spectrometry device of the present invention utilizes a filter in the form of a carbon foil interposed between the surface of a workpiece and the detector which is operable to trap backscattered ions from the workpiece. With this arrangement, only the ions backscattered by the atoms heavier that the known atoms of the workpiece are received and counted by the detector. Since the detector only counts the ions backscattered by the unknown heaver impurities, pulse pileup rejection circuitry and a cooling system for the detector are not required.

Accordingly, the present invention is directed to a backscattering spectrometry device for identifying unknown contaminant elements present in a workpiece. The backscattering spectrometry device comprises an ion beam which impacts the surface of a workpiece and collides with the known atoms of the workpiece and with unknown atoms of any impurity also present in the workpiece, which beam thereafter backscatters away from the workpiece, and a filter in the form of a range foil to stop the backscattered ions backscattered from the known atoms of the workpiece while permitting the ions backscattered from the heavier impurities to pass, and a detector means to count the number of events (an event occurring when an ion passes through the foil filter and reaches the detector) and to measure the energy of the backscattered ions to determine the mass of and identify the the unknown impurities. We refer to this analyses as Heavy Ion Backscattering Spectrometry or HIBS.

In the preferred embodiment, the impacting energy beam has an energy between one hundred and eight hundred KeV composed of ions used for implantation processes during the manufacture of semiconductor devices. Typically, such beam may be oxygen, nitrogen, boron, carbon, fluorine, or neon ions. Further, it is preferred that the ranging foil filter be self-supporting and be sufficiently thick to trap therewithin substantially all of the backscattered ions after impact with the unknown contaminants. Preferably, the foil is comprised of carbon and is between fifty and five hundred nanometers thick.

Further, the present invention is directed to a method for identifying and measuring the relative concentration of unknown elements present in a workpiece comprising the steps of directing an ion beam to the surface of a workpiece, which beam impacts the surface of said workpiece and collides with known and unknown atoms in the workpiece and backscatter though a scattering angle realign from those collisions, filtering, using a range foil, those ions backscattered from collisions with atoms of known composition which pervade the workpiece and passing through the filter those ions backscattered from collisions with unknown atoms in the workpiece, and counting the number of events which signify that an ion which has collide with an unknown atom present in the workpiece has passed through the filter measuring the energy of that ion to determine the mass of and thereby identify the unknown elements present in the workpiece.

Preferably, the method of the invention is employed in-situ, i.e., while the workpiece is being implanted with an ion beam as a process or manufacture step. More preferably, the HIBS method of the invention employs an oxygen ion beam during the implantation of oxygen onto a silicon wafer during the manufacture of silicon-on-insulator regions on the wafer.

These and other features and advantages of the present invention will become apparent to those skilled in the art upon reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

In the following description, it is to be understood that such terms as "forward", "rearward", "left", "right", "upwardly", "downwardly", and the like, are words of convenience and are not to be construed as limiting terms.

In General

Figure 1:
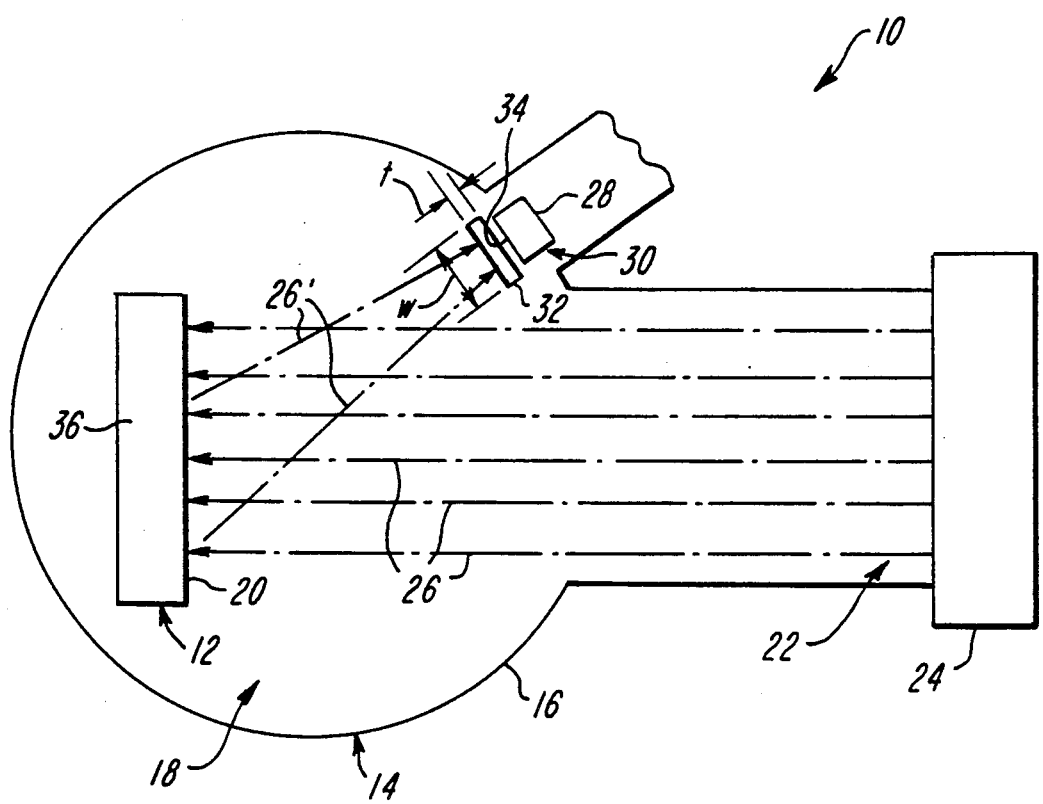
FIG. 1 is a schematic diagram of backscattering spectrometry device of the present invention, illustrating an ion beam source projecting an ion beam that impacts the surface of a workpiece. Atoms of the workpiece and atoms of any unknown elements present in the workpiece backscatter a portion of the incident ion beam. Also shown is a filter for separating ions backscattered by the workpiece atoms from those ions backscattered by the unknown atoms also present in the workpiece. A detector counts the ions backscattered from the unknown atoms and measures their energies which allows for the identification of the contaminant elements present in the workpiece.

Referring now to the drawings, and particularly to FIG. 1, where there is shown schematically a backscattering spectrometry device, generally designated by the numeral 10, which is the subject of the present invention. The method of the invention will herein be referred to as "HIBS", an acronym for Heavy Ion Backscattering Spectrometry. As will be described herein, the spectrometry device 10 is operable to identify unknown elements present in a workpiece 12, such as a silicon wafer or other desired material. For a general discussion of the backscattering spectrometry device described herein, reference is made to two articles by the co-inventors: (1) "Heavy-Ion Backscattering Spectrometry (HIBS) for High-Sensitivity Surface Impurity Detection," *Nuclear Instruments and Methods in Physics Research*, Vol. B45, pp. 143-146 (1990); and (2) "Heavy Ion Backscattering Spectrometry (HIBS) - An Improved Technique for Trace Element Detection" *Nuclear Instruments and Methods in Physics Research*, Vol. B42, pp. 295-297 (1989), which articles are hereby incorporated by reference.

The principles underlying any backscattering spectrometry device are based on conservation of momentum and energy between particles in an elastic collision. An elastic collision is one wherein the kinetic energy remains unchanged. Thus, when an ion beam having a known mass and a known energy collides with a particle of unknown mass, the known particle rebounds at a selected scattering angle with a different energy. Conservation equations state that the momentum and the kinetic energy of the two particles before the collision are equal to the momentum and kinetic energy of the two particles after the collision. In this instance, the collisions of interest are the collisions between ions in the incident beam and between atoms in the workpiece. The ions within the beam have a known energy and a known mass prior to the collision with a particle of unknown mass. After and resulting from the collision, the energy of the backscattered ion has changed and this measurable energy change is related to the scattering angle and the mass of the unknown particle, which can be calculated, and the impurity identified.

There will be different species of atoms in a workpiece. Those atoms that comprise the majority of atoms in the workpiece itself, such as silicon atoms of a silicon substrate, will be referred to as the workpiece atoms. Other atoms, not of the same species as the bulk of the workpiece are impurities because they differ from the workpiece atoms, not necessarily because they are unwanted. There may be some desirable impurities or contaminants necessary to the function of the microelectronics manufactured. The method and device of the invention is capable of detecting all impurities with a mass greater than argon with a sensitivity proportional to the square of the atomic number of the impurity.

Practicably, however, the efficacy and sensitivity of the device and method of the invention is limited by the relationship between the atomic number, Z, and energy, E, of the incident ion beam — $(Z/E)^2$. Thus, as the atomic number of the incident ion beam decreases or as the energy of the beam increases, there is a corresponding loss of sensitivity. But as the mass of the beam which is proportional to Z increases, the resolution or the ability to distinguish between different kinds of elements within the workpiece diminishes.

The backscattering spectrometry device 10 of the present invention includes a chamber 14 having a continuous wall 16 defining a hollow interior 18. The workpiece 12 is disposed in the hollow interior 18 of the chamber 14 and positioned so that the surface 20 of the workpiece 12 faces a first opening 22 formed in the wall 16 of the chamber 14. A conventional ion beam source 24 is positioned in the first opening 22 for communication with the interior 18 of the chamber 14 and is operable to project or emit an ion beam through the hollow interior 18 to impact the workpiece 12. Preferably, the ion beam source 24 emits an ion beam 26 having an energy between one hundred (100) and eight hundred (800) KeV and is composed of oxygen, carbon, nitrogen, boron, neon, or fluorine. Any species of ion beam heavier than the atoms of interest in the workpiece to be analyzed may be used, but as previously stated, the ease of particle filtering and detection becomes more difficult as the mass of the incident ions increase. The sensitivity of the method will also vary according to the relationship between the atomic number and energy of the beam, $(Z/E)^2$.

The backscattering spectrometry device 10 further includes a conventional detector 28 disposed in a second opening 30 defined in the chamber wall 16. The detector is positioned at a predetermined angle, the "scattering angle", relative to the normal of the surface 20 of the workpiece 12. The scattering angle is critical in the determination of the mass of the impurity atoms, using the measured energy of the backscattered ion. The detector 28 receives ions backscattered from collisions with an unknown impurity within the workpiece and then counts the number of events when a backscattered ion reaches the detector. The ion beam 26 backscattered from surface 20 of workpiece 12 at the scattering angle is designated by the number 26' in FIG. 1.

The backscattering spectrometry device 10 finally includes a filter 32 disposed within the hollow interior 18 of the chamber 14 and interposed between the workpiece 12 and the detector 28. The filter 32 is a self-supporting foil having a preselected thickness "t" and with an overall width "w" selected to span across the entire ion-receiving surface 34 of the detector 28. It is well known that as ions pass through a foil, they lose energy equal to the product of the stopping cross section of the foil, the atomic density of the foil and the thickness of the foil. Thus, the foil can be chosen to selectively stop ions of a particular energy, such as those ions which backscatter from the workpiece substrate itself. As seen, the foil filter 32 is positioned at the scattering angle to receive the ions backscattered, shown as 26', from the surface 20 of the workpiece 12.

Operation of the Backscattering Spectrometry Device of the Present Invention

As mentioned earlier, the ion beam source 24 positioned within the first opening 22 of the wall 16 for communication with the hollow interior 18 of the chamber 14 emits an ion beam 26 having an energy level of between one hundred (100) and eight hundred (800) KeV through the hollow interior 18 to impact the surface 20 of the workpiece 12. Typically, the ion beam 26, of an energy level between one hundred (100) and eight hundred (800) KeV, does not actually rebound from the surface of workpiece 12, but penetrates the surface 20 of the workpiece 12. Of course, the depth of penetration is dependent upon the incident energy of the ion beam 26. As the ion beam 26 impacts the surface 20 of the workpiece 12 and penetrates into the workpiece interior 36, a portion of beam 26 collide with atoms comprising the workpiece 36. As a result of the elastic collisions, the ions are backscattered from atoms of workpiece 12 and atoms of any unknown impurities (not shown) within the penetration range of the ion beam 26. The ions backscattered from these collisions reflect in all directions and so only a portion of the backscattered ions rebound through the scattering angle toward the detector 28.

As the backscattered ion beams 26' travels towards the detector 28, it first contacts the foil filter 32 interposed between the workpiece 12 and the detector 28. As the ions pass though the foil 32, they lose kinetic energy as discussed earlier. Because of the kinematics, ions which have been backscattered as a result of collisions with heavier unknown impurities have greater kinetic energy and pass through the carbon foil filter 32 to be received by the detector 28. For example, with a 400 KeV incident beam of carbon ions, a carbon foil with a thickness of forty micrograms per square centimeter is selected to stop most of the particles scattered from collisions with silicon molecules in a silicon workpiece 12. If the silicon workpiece 12 is contaminated with traces of gold, the ions backscattered as a result of collisions with the gold atoms have more kinetic energy and will pass through the carbon foil filter 32 and be received by the detector 28. The detector 28 counts the number of events, an event occurring when an ion reaches the detector, and the detector also measures the energy of the ion. As explained earlier, from momentum and energy conservation principles, if the mass and the energy of the backscattered ions are known, the mass of the unknown impurities within the workpiece can be determined to identify that element.

Figure 2:
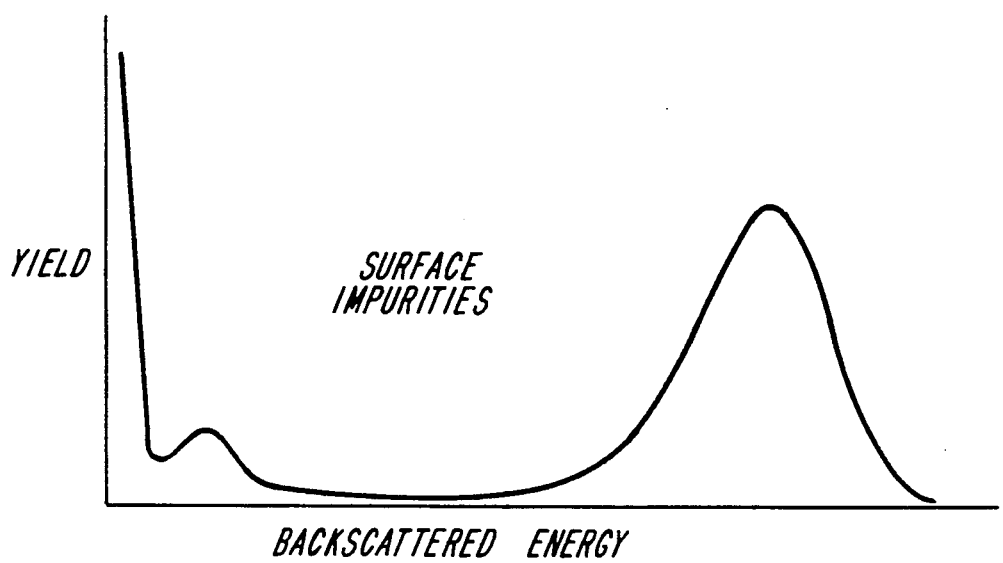
FIG. 2 is a graph illustrating the magnitude of two separate contaminant elements present in a workpiece and detected by the backscattering spectrometry device of the present invention.

It has been shown that the backscattering spectrometry device schematically shown in FIG. 1 with a 400 KeV carbon ion beam incident upon a silicon workpiece 12, utilizing a carbon foil filter, has a sensitivity to detect contaminants with a mass greater then the mass of silicon of $10^{11}$ atoms/cm$^2$. It is apparent that the sensitivity of the backscattering spectrometry device 10 of FIG. 1 including the carbon foil filter 32 is greater than the sensitivity of a conventional Rutherford Backscattering Spectrometry device, which has a sensitivity of $10^{13}$ for heavy contaminant impurities present in a silicon wafer workpiece. Further, the backscattering spectrometry device schematically shown in FIG. 1 detects all unknown impurities having a mass heavier than argon. The events, or the number of backscattered ions from collisions with the unknown impurities counted by the detector 28, is plotted on a graph as shown in FIG. 2. This figure illustrates the relative concentrations of the different impurities identified as being present in the workpiece 12.

The use of HIBS for ultratrace impurity detection on light substrates is a useful technique, with potential applications ranging from microelectronics to fields as diverse as geochemistry and environmental sciences. The use of a ranging foil in front of the detector simplifies and speeds data collection by eliminating pileup resulting from scattering from the substrate. The primary advantage of the technique is the ability to detect with good sensitivity all elements a few atomic mass units heavier than that of the substrate. Other trace-element analyses such as SIMS have particular difficulty with certain elements such as $^{56}$Fe on $^{28}$Si.

It is apparent from the above discussion that the backscattering spectrometry device 10 of the present invention may be used as a manufacturing device which also provides an in-situ diagnostic for contaminants element detection and control. For example, if the workpiece 12 is a silicon wafer and the ion beam 26 is an oxygen ion beam having an energy level of between one hundred (100) and eight hundred (800) KeV, the same ion beam 26 used to implant oxygen ions to form an oxide layer in the interior of the silicon wafer to produce a silicon-on-insulator (SOI) wafer is also used to detect atoms of unknown impurities present in the silicon wafer. By identifying the impurities present in the silicon wafer workpiece, the source of the impurities may be isolated and eliminated to prevent further contamination during the SOI manufacturing process. The device 10 could also be used as an in-situ impurity diagnostic during routine boron dopant implants of silicon integrated circuits. As with the SOI processing application described above, the implantation beam doubles as a probe beam whose backscattering provides the signals required to identify and quantify impurities introduced to the integrated circuit during previous process steps or during the implantation step itself.

It is thought that the present invention and many of its attendant advantages will be understood from the foregoing description and it will be apparent that various changes may be made in the form, construction and arrangement thereof without departing from the spirit and scope of the invention or sacrificing all of its material advantages, the form hereinbefore described being merely a preferred or exemplary embodiment thereof.

We claim:

1. A backscattering spectrometry device for identifying and determining the amount of unknown elements in a workpiece, comprising:
   (a) an ion beam impacting a surface of and penetrate a workpiece to collide with known atoms and unknown atoms in said workpiece resulting in a backscattered beam from said surface away from said workpiece;
   (b) filter means for stopping said backscattered ions which collided with known atoms in said workpiece while said backscattered ions which collided with unknown atoms in said workpiece pass through said filter means; and
   (c) detector means for counting the number and measuring the energy of said backscattered ions which collided with unknown atoms in said workpiece to determine the mass of said unknown atoms in said workpiece to thereby identify and determine the concentration of said unknown atoms in said workpiece.

2. The backscattering spectrometry device as recited in claim 1, wherein said ion beam has an energy between one hundred and eight hundred KeV.

3. The backscattering spectrometry devices as recited in claim 2, wherein said ion beam is comprised of ions of one of the following group: carbon, nitrogen, oxygen, boron, fluorine or neon.

4. The backscattering spectrometry device as recited in claim 1, wherein said filtering means further comprises a self-supporting foil having a preselected thickness, a preselected cross section and a preselected atomic density and is positioned between said workpiece and said detector means so as to stop said backscattered ions which collided with known atoms in said workpiece, but to pass said backscattered ions which collided with unknown atoms in said workpiece.

5. The filtering means as recited in claim 4, wherein said filtering means is a carbon foil having said predetermined thickness between fifty and five hundred nanometers.

6. The backscattering spectrometry device as recited in claim 1, further comprising:
   (a) a chamber formed by a continuous wall defining a hollow interior and having first and second openings defined in said wall and being spaced from one another;
   (b) said workpiece being disposed within said hollow interior of said chamber and so oriented such that a surface of said workpiece faces toward said first opening defined in said chamber wall;
   (c) said ion beam being provided by an ion beam source positioned in said first opening and so oriented to emit said ion beam through said hollow interior of said chamber and toward said surface of said workpiece;
   (d) said detector means being positioned in said second opening and so oriented to receive said backscattered ion beam from said workpiece surface; and
   (e) said filter means being disposed within said hollow interior of said chamber and interposed between said workpiece surface and said detector means.

7. The backscattering spectrometry device as recited in claim 1, wherein:
   said workpiece is a silicon wafer; and
   said ion beam is a one hundred to eight hundred KeV heavy oxygen (O+) ion beam which impacts said silicon wafer surface and implants said oxygen ions in said wafer thereby forming a silicon-on-insulator region in said silicon wafer.

8. A backscattering spectrometry device for identifying unknown elements, comprising:
   (a) a workpiece disposed within a chamber formed by a continuous wall having first and second openings defined in said wall;
   (b) an ion beam source disposed in said first opening of said chamber wall and adapted to emit a ion beam for impacting a surface of said workpiece and penetrating said workpiece resulting in collisions between said ion beam and known atoms and said unknown elements of said workpiece; said ion beam backscattering through a scattering angle away from said workpiece;
   (c) a carbon foil filter between fifty and five hundred nanometers thick disposed in said chamber for receiving said backscattered ion beam, said carbon foil filter being operable to stop said backscattered ions which collided with known atoms in said workpiece, while passing said backscattered ions which collided with said unknown elements; and (d) an ion detector disposed in said second opening of said chamber wall and positioned along said scattering angle to receive said backscattered ions which collided with unknown elements within said workpiece which passed through said carbon foil filter, said detector being operable to count the number of said ions and to measure the energy of said ions to thereby identify and quantify said unknown elements present in said workpiece.

9. The backscattering spectrometry device as recited in claim 8, wherein said workpiece is a silicon wafer.

10. The backscattering spectrometry device as recited in claim 8, wherein said ion beam has an energy between one hundred and eight hundred KeV and is selected from the group consisting of carbon, oxygen, nitrogen, boron, fluorine or neon.

11. A method for identifying and measuring the relative concentration of unknown elements present in a workpiece, comprising the steps of:

(a) impacting the surface of said workpiece with an ion beam of known energy thereby effecting collisions of said ion beam with known atoms and unknown elements in said workpiece, said ion beam backscattering away from said workpiece as a result of said collisions;

(b) filtering said backscattered ion beam to remove said ions which collided with said known atoms and passing said backscattered ion beam which collided with said unknown elements; and (c) counting the number and measuring the energy of said backscattered ions which collided with unknown elements in said workpiece; and (d) determining the identify and relative concentration of said unknown elements present in said workpiece.

12. The method as recited in claim 11, wherein said filtering step includes:

stopping said backscattered ion beam in a foil whose composition, density and thickness is chosen to stop said ions which collided with said known atoms in said workpiece while permitting said backscattered ion beam which collided with unknown elements to pass through said foil filter.

13. The method as recited in claim 11, wherein said method occurs during ion implantation of said workpiece during manufacture.

14. A method for identifying and measuring the relative concentration of unknown elements present in a silicon workpiece, comprising the steps of:

(a) implanting said workpiece with an oxygen ion beam of energy between one hundred and eight hundred KeV to create a silicon-on-insulator region in said workpiece, wherein said beam also collides with known silicon atoms and unknown elements in said silicon workpiece; said ion beam backscattering away from said workpiece as a result of said collisions;

(b) filtering said backscattered ion beam directed along a scattering angle by stopping said backscattered ion beam in a carbon foil between fifty and five hundred nanometers thick, said foil permitting said backscattered ion beam which collided with unknown elements to pass through said foil filter; and (c) counting the number and measuring the energy of said backscattered ions which have passed through said foil and reach a detector means; and (d) determining the identify and relative concentration of said unknown elements present in said workpiece.

* * * * *